(12) United States Patent
Kauffman

(10) Patent No.: US 9,546,126 B2
(45) Date of Patent: Jan. 17, 2017

(54) NATURAL BASED BRANCHED COMPOSITIONS

(71) Applicant: Armstrong World Industries, Inc., Lancaster, PA (US)

(72) Inventor: William J. Kauffman, Manheim, PA (US)

(73) Assignee: AFI Licensing LLC, Lancaster, PA (US)

( * ) Notice: Subject to any disclaimer, the term of this patent is extended or adjusted under 35 U.S.C. 154(b) by 672 days.

(21) Appl. No.: 13/946,683

(22) Filed: Jul. 19, 2013

(65) Prior Publication Data

US 2014/0031570 A1    Jan. 30, 2014

Related U.S. Application Data

(60) Provisional application No. 61/741,605, filed on Jul. 24, 2012.

(51) Int. Cl.
| | | |
|---|---|---|
| C07C 69/732 | (2006.01) | |
| C08L 101/08 | (2006.01) | |
| C09F 7/00 | (2006.01) | |
| C08L 101/00 | (2006.01) | |
| B32B 27/00 | (2006.01) | |
| B32B 27/08 | (2006.01) | |

(52) U.S. Cl.
CPC .......... C07C 69/732 (2013.01); C08L 101/005 (2013.01); C08L 101/08 (2013.01); C09F 7/00 (2013.01); B32B 27/00 (2013.01); B32B 27/08 (2013.01)

(58) Field of Classification Search
CPC ................. B32B 27/00; B32B 27/08
See application file for complete search history.

(56) References Cited

U.S. PATENT DOCUMENTS

| | | | | |
|---|---|---|---|---|
| 1,576,181 | A * | 3/1926 | Dubsky | D06N 1/00 106/253 |
| 2,786,773 | A * | 3/1957 | Bradley, Jr. | C08G 59/1472 106/223 |
| 2,815,295 | A * | 12/1957 | Forsythe | D06N 1/00 106/164.43 |
| 2,936,244 | A * | 5/1960 | Ayers | D06N 1/00 106/223 |
| 5,026,770 | A | 6/1991 | Smeets et al. | |
| 5,663,247 | A * | 9/1997 | Sorensen | C08G 63/20 424/DIG. 16 |
| 2009/0314180 | A1 * | 12/2009 | Peterson | C08G 63/48 106/31.6 |

FOREIGN PATENT DOCUMENTS

| | | |
|---|---|---|
| EP | 0377258 | 7/1990 |
| WO | 2012/094601 | 7/2012 |

OTHER PUBLICATIONS

Wicks, Z.W., Drying Oils, 2002, Kirk-Othmer Encyclopedia of Chemical Technology, Wiey & Sons, Inc., vol. 9, 3 pages.*
European Search Report dated Dec. 3, 2013, for EP Publication No. 13177206, filed Jul. 17, 2013. EP.

* cited by examiner

Primary Examiner — Yate K Cutliff

(57) ABSTRACT

A linoleum composition including a dendritic substituent comprising (i) a polyfunctional core including a plurality of primary branches extending from the core and (ii) a plurality of dendritic branches extending from the plurality of primary branches, and each dendritic branch having an unsaturated functionality.

17 Claims, No Drawings

NATURAL BASED BRANCHED COMPOSITIONS

CROSS-REFERENCE TO RELATED APPLICATIONS

This patent application claims the benefit of U.S. Provisional Patent Application Ser. No. 61/741,605 filed on Jul. 24, 2012, and entitled "NATURAL BASED BRANCHED COMPOSITIONS" the disclosure of which is incorporated by reference as if fully rewritten herein.

FIELD OF THE INVENTION

The present invention relates to linoleum formulations and linoleum compositions.

BACKGROUND OF THE INVENTION

Linoleum compositions have been useful as flooring materials for quite a long time. Over the years, improvements in curing of linoleum compositions have been made. However, the current linoleum flooring process still requires upward of two weeks or longer to reach acceptable curing properties for use as a floor.

There is a need for natural based, renewable compositions such as linoleum that have a more efficient manufacturing process and improved performance.

In particular, there is a need in the art for linoleum formulations and compositions that require reduced, preferably significantly reduced, curing times as compared to current commercially available linoleum formulations and compositions. There is also a need in the art for linoleum formulations and compositions that can be efficiently cured without requiring any additional heat input, known in the art as stoving.

SUMMARY OF THE INVENTION

In one aspect, the present invention provides a linoleum composition including a dendritic substituent comprising (i) a polyfunctional core including a plurality of primary branches extending from the core and (ii) a plurality of dendritic branches extending from the plurality of primary branches, and each dendritic branch having an unsaturated functionality.

In some embodiments, the polyfunctional core is derived from a polyglyceride of one or more first unsaturated fatty acids. In some embodiments, the polyglyceride comprises a triglyceride. In some embodiments, the one or more first unsaturated fatty acids comprise one or more C16 to C20 unsaturated fatty acids, for example at least one C18 fatty acid, typically linoleic acid.

In some embodiments, the polyglyceride is derived from linseed oil and comprises derivatives of linoleic, oleic and alpha-linoleic acid.

In some embodiments, the dendritic branch is derived from at least one second unsaturated fatty acid. In some embodiments, the at least one second unsaturated fatty acid is selected from a C16 to C20 unsaturated fatty acid, for example a C18 unsaturated fatty acid, typically linoleic acid.

In some embodiments, each dendritic branch includes a first branch substituent derived from at least one third unsaturated fatty acid and having an unsaturated functionality, and a second dendritic substituent pendant from the first dendritic substituent, the second dendritic substituent being derived from at least one fourth unsaturated fatty acid and having an unsaturated functionality. In some embodiments, the dendritic branch comprises unsaturated fatty acid ester. In some embodiments, at least one or both of the third and fourth unsaturated fatty acids is a C16 to C20 unsaturated fatty acid, for example a C18 unsaturated fatty acid, typically linoleic acid.

In some embodiments, the dendritic branch has a hydroxyl functionality,

In some embodiments, each dendritic branch has a tertiary substituent derived from reaction, with a hydroxyl functionality on the dendritic branch, of a capping component selected from at least one of the group consisting of an acid, an acid anhydride, an acid chloride, an isocyanate and a silicon-containing material.

In some embodiments, each dendritic branch is cross-linked to a further dendritic branch by a cross-linking substituent derived from reaction, with a hydroxyl functionality on the cross-linked dendritic branches, of a cross-linking component selected from at least one of the group consisting of a melamine, an isocyanate and a silicon-containing material.

In some embodiments, the linoleum composition further comprises at least one of linseed oil and oxidized linseed oil, and the dendritic substituent comprises from 5 to 75 wt %, optionally from 20 to 35 wt %, based on the total weight of the at least one of linseed oil and oxidized linseed oil in the linoleum composition.

In another aspect, the present invention provides a method of manufacturing a linoleum composition, the method including the steps of:

(a) providing a polyfunctional core including a plurality of primary branches extending from the core; and (b) reacting at least one unsaturated substituent onto the primary branches to form a dendritic substituent comprising a plurality of dendritic branches extending from the plurality of primary branches, each dendritic branch having an unsaturated functionality.

In some embodiments, the polyfunctional core is derived from a polyglyceride of one or more first unsaturated fatty acids. In some embodiments, the polyglyceride comprises a triglyceride. In some embodiments, the one or more first unsaturated fatty acids comprise one or more C16 to C20 unsaturated fatty acids for example at least one C18 fatty acid typically linoleic acid.

In some embodiments, the polyglyceride is derived from linseed oil and comprises derivatives of linoleic, oleic and alpha-linoleic acid.

In some embodiments, each primary branch of the polyfunctional core includes at least one epoxy functional group and in step (b) the unsaturated substituent is reacted with an epoxy functional group. In some embodiments, the at least one unsaturated substituent comprises a second unsaturated fatty acid to form the dendritic branch. Optionally, the second unsaturated fatty acid is selected from a C16 to C20 unsaturated fatty acid, for example a C18 unsaturated fatty acid, typically linoleic acid.

In some embodiments, step (b) comprises a sub-step (b1) wherein a third unsaturated fatty acid is reacted with the primary branch to form a first dendritic substituent, having an unsaturated functionality, of the dendritic branch, and a sub-step (b2) wherein a fourth unsaturated fatty acid is reacted with the first dendritic substituent to form a second dendritic substituent pendant from the first dendritic substituent, the second dendritic substituent having an unsaturated functionality.

In some embodiments, the dendritic branch comprises unsaturated fatty acid ester. In some embodiments, at least one or both of the third and fourth unsaturated fatty acids is a C16 to C20 unsaturated fatty acid, for example a C18 unsaturated fatty acid, typically linoleic acid.

In some embodiments, the dendritic branch has a hydroxyl functionality.

In some embodiments, after step (b) each dendritic branch has at least one hydroxyl functionality and further comprising step (c) of reacting a capping component selected from at least one of the group consisting of an acid, an acid anhydride, an acid chloride, an isocyanate and a silicon-containing material with the hydroxyl functionality to form a tertiary substituent of the dendritic branch.

In some embodiments, after step (b) each dendritic branch has at least one hydroxyl functionality and further comprising step (d) of reacting a cross-linking component selected from at least one of the group consisting of a melamine, an isocyanate and a silicon-containing material with the hydroxyl functionality to cross-link the dendritic branch to a further dendritic branch.

In some embodiments, the linoleum composition further comprises at least one of linseed oil and oxidized linseed oil and the dendritic substituent comprises from 5 to 75 wt %, optionally from 20 to 35 wt %, based on the total weight of the at least one of linseed oil and oxidized linseed oil in the linoleum composition.

In some embodiments, the method further comprises the step, after step (b), of pre-oxidizing the linoleum composition produced in step (b) during a linoleum manufacturing process.

In some embodiments, the method further comprises the step, after step (b), of adding the linoleum composition produced in step (b) to an oxidized linoleum cement formulation.

In another aspect, the present invention provides a linoleum formulation with improved curing time comprising a dendritic or branched composition having pendant olefin functionality.

Optionally, the dendritic or branched composition comprises unsaturated fatty acid ester.

In another aspect, the present invention provides a dendritic or branched composition that improves curing time when incorporated into a linoleum formulation. Optionally, the dendritic or branched composition is incorporated into the linseed oil pre-oxidation step of the linoleum process.

In another aspect, the present invention provides a dendritic or branched composition based upon an epoxidized core and unsaturated fatty acids. Optionally the epoxidized core is an epoxidized triglyceride of unsaturated fatty acid or is epoxidized linseed oil.

In another aspect, the present invention provides a linoleum composition comprising an additional curable component comprising a dendritic or branched composition having a reactive olefin functionality capable of cross-linking via free radical mechanism.

Optionally, the reactive olefin functionality is obtained by capping the dendritic or branched compositions comprising hydroxyl groups.

In some embodiments, the dendritic or branched composition is present during the pre-oxidation step of the linoleum process.

In some embodiments, the dendritic or branched composition is added to an oxidized linoleum cement formulation.

In another aspect, the present invention provides a natural based composition useful as a flooring component comprising a dendritic or branched composition having pendant olefin functionality.

In some embodiments, the composition is curable via a dual curing process comprising a first curing step reacting together the pendant olefin functionality and a second curing step reacting a different functionality in the a dendritic or branched composition, the first and second curing steps being alternative or additive and carried out in any order or simultaneously.

In some embodiments, the dendritic or branched composition further comprises hydroxyl functionality. Optionally, the hydroxyl functionality is used to cross-link the composition.

In another aspect, the present invention provides a flooring product comprising the linoleum composition or the linoleum formulation of the present invention or the linoleum composition produced according to the method of the present invention.

This invention is at least partly predicated upon the finding that the use of dendritic or branched compositions based upon natural, renewable compositions can be used in combination with linseed oil to provide more efficient linoleum curing cycles. Furthermore, it has been found that such compositions permit the utilization of a dual cure mechanism for linoleum that provides improved curing rate and improved performance. Although preferred to be used in combination with linseed oil, the dual cure compositions have utility without the need to combine with linseed oil.

DETAILED DESCRIPTION OF THE INVENTION

This invention describes the use of dendritic or branched compositions that are based on natural materials that find utility in various applications, including preparation of linoleum compositions with significantly reduced curing times.

The linoleum composition of the invention in some embodiments includes a dendritic substituent comprising (i) a polyfunctional core including a plurality of primary branches extending from the core and (ii) a plurality of dendritic branches extending from the plurality of primary branches, and each dendritic branch having an unsaturated functionality The linoleum composition may be manufacture by a method including the steps of:
(a) providing a polyfunctional core including a plurality of primary branches extending from the core; and
(b) reacting at least one unsaturated substituent onto the primary branches to form a dendritic substituent comprising a plurality of dendritic branches extending from the plurality of primary branches, each dendritic branch having an unsaturated functionality.

In some embodiments, the polyfunctional core is derived from a polyglyceride of one or more first unsaturated fatty acids. In some embodiments, the polyglyceride comprises a triglyceride. In some embodiments, the one or more first unsaturated fatty acids comprise one or more C16 to C20 unsaturated fatty acids, for example at least one C18 fatty acid, typically linoleic acid.

In one embodiment, a natural based triglyceride of linoleic acid is epoxidized, with each original double bond olefinic unsaturation being epoxidized. There are six epoxide groups, two on each linoleic branch. The triglyceride with the epoxidized linoleic branches comprises a polyfunctional core including a plurality of primary branches extending from the core.

In some embodiments, the dendritic branch is derived from at least one second unsaturated fatty acid. In some embodiments, the at least one second unsaturated fatty acid is selected from a C16 to C20 unsaturated fatty acid, for example a C18 unsaturated fatty acid, typically linoleic acid.

Accordingly, in this embodiment the epoxidized triglyceride is subsequently reacted with linoleic acid, as shown in reaction A below.

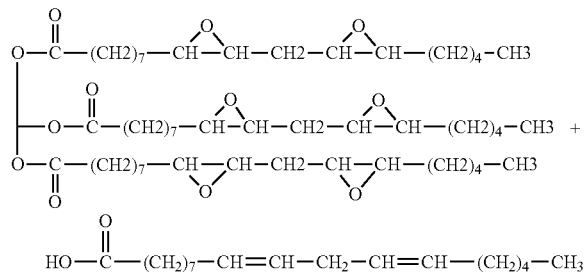

In reaction A one linoleic acid molecule reacts with each epoxy group in the linoleic branches to produce a plurality of dendritic branches extending from the plurality of primary branches, and each dendritic branch has an unsaturated functionality derived from the respective linoleic acid molecule. This reaction produces what is termed herein as a "level 1" dendritic-type molecule (hereinafter called "Composition I") having 6 secondary hydroxyl groups (one in each linoleic acid derivative dendritic branch where the carboxylic group of the acid reacted with the respective epoxide group) and 12 olefin functional groups (two in each linoleic acid derivative dendritic branch). There are six dendritic branches, two extending from each primary branch. Composition I is shown below.

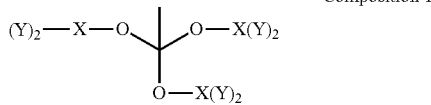
Composition 1 where
X=—C(O)—(CH$_2$)$_7$—CH(OH)—CH(OY)—CH$_2$—CH(OH)—CH(OY)—(CH$_2$)$_4$—CH$_3$
Y=—C(O)—(CH$_2$)$_7$—CH=CH—CH$_2$—CH=CH—(CH$_2$)$_4$—CH$_3$ In some embodiments, each dendritic branch includes a first branch substituent derived from at least one third unsaturated fatty acid and having an unsaturated functionality, and a second dendritic substituent pendant from the first dendritic substituent, the second dendritic substituent being derived from at least one fourth unsaturated fatty acid and having an unsaturated functionality. In some embodiments, the dendritic branch comprises unsaturated fatty acid ester. In some embodiments, at least one or both of the third and fourth unsaturated fatty acids is a C16 to C20 unsaturated fatty acid, for example a C18 unsaturated fatty acid, typically linoleic acid.

In some embodiments, the dendritic branch has a hydroxyl functionality, which may be provided by secondary hydroxyl groups.

Accordingly, in another embodiment, these secondary hydroxyl groups are esterified with additional linoleic acid to produce a level 1 dendritic molecule having 24 olefin functional groups, shown as Composition III below).

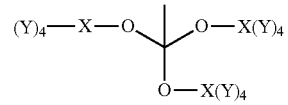
Composition III where
X=—C(O)—(CH$_2$)$_7$—CH(OY)—CH(OY)—CH$_2$—CH(OY)—CH(OY)—(CH$_2$)$_4$—CH$_3$
Y=—C(O)—(CH$_2$)$_7$—CH=CH—CH$_2$—CH=CH—(CH$_2$)$_4$—CH$_3$ In other embodiment, epoxidized linseed oil is employed as the core material in the preparation of an asymmetrical dendritic or branched molecule—Composition II.

In some embodiments, the polyglyceride is derived from linseed oil and comprises derivatives of linoleic, oleic and alpha-linoleic acid. Accordingly, in another embodiment, linseed oil is used as a precursor to form a polyfunctional core including a plurality of primary branches extending from the core.

Linseed oil is comprised of a triglyceride mixture comprising mainly oleic acid, linoleic acid and alpha-linolenic acid. As for the production of Composition I, the unsaturated olefinic groups in linseed oil are initially epoxidized and then the epoxide groups are reacted with linoleic acid, each carboxylic group in a respective linoleic acid molecule reacting with a respective epoxide group. Such sequential reactions produce another dendritic substituent, with the linoleic acid derivatives forming the dendritic branches, called herein Composition IV. Composition I is symmetrical because there are two dendritic branches on each primary branch, each dendritic branch located at a respective unsaturated site in the original triglyceride precursor, whereas Composition IV is asymmetrical because there are different numbers of dendritic branches on each primary branch, as a result of the different unsaturation and location of the unsaturated olefinic bonds in the oleic acid, linoleic acid and alpha-linolenic acid derivatives in the linseed oil.

In the formation of a level 1 dendritic substituent, at least one unsaturated substituent is reacted onto the primary branches to form a dendritic substituent comprising a plurality of dendritic branches extending from the plurality of primary branches, each dendritic branch having an unsaturated functionality. In the formation of a "level 2" dendritic substituent, in a first sub-step a third unsaturated fatty acid is reacted with the primary branch to form a first dendritic substituent, having an unsaturated functionality, of the dendritic branch, and in a subsequent second sub-step a fourth unsaturated fatty acid is reacted with the first dendritic substituent to form a second dendritic substituent pendant from the first dendritic substituent, the second dendritic substituent having an unsaturated functionality.

In a further embodiment, a "level 2" dendritic or branched composition is produced. For example, epoxidation of Composition III followed by reaction with linoleic acid produces a level 2 dendritic molecule having 24 secondary hydroxyl groups and 48 olefin functional groups. Further esterification of the hydroxyl groups with linoleic acid produces a level 2 dendritic molecule having 96 olefin functional groups.

It is also to be understood that the dendritic or branched compositions containing hydroxyl and olefin functional groups can be epoxidized and further reacted with linoleic acid. Additionally, these epoxidized compositions can be further cross-linked to produce useful end products.

These types of dendritic or branched compositions are more rapidly cured than linseed oil itself, in particular during the manufacture of linoleum compositions. Addition of these dendritic or branched compositions materials into the linseed oil oxidation step of a conventional linoleum production process, or the addition of these dendritic or branched compositions materials into oxidized linoleum cement mixtures, can significantly reduce the curing time for linoleum products.

In some embodiments, the linoleum composition further comprises at least one of linseed oil and oxidized linseed oil, in addition to the dendritic substituent.

The percentage of these dendritic or branched compositions based upon the amount of linseed oil present in a linoleum composition can vary widely depending upon application and processing differences. Typically, when incorporated in a linoleum composition these dendritic or branched compositions are present in the range of from 5% to 75 wt %, preferably from 20% to 35%, based on the weight of linseed oil and/or oxidized linseed oil in the linoleum composition.

Although the above-described embodiments employ linoleic acid as a precursor for the dendritic branches, it is to be understood that other natural unsaturated fatty acids or mixtures of fatty acids can be employed in place of, and/or additional to, linoleic acid to make the dendritic or branched compositions. For example, the unsaturated fatty acid is selected from a C16 to C20 unsaturated fatty acid, for example a C18 unsaturated fatty acid, typically linoleic acid.

Secondary hydroxyl groups result from the reaction of the fatty acid dendritic branch precursors with the epoxide groups either on the primary branches or, after subsequent epoxidization, on the dendritic branches. Such secondary hydroxyl groups are sites for reactions with other acids, or anhydrides to modify the dendritic or branched structure.

In some embodiments, each dendritic branch has a tertiary substituent derived from reaction, with a hydroxyl functionality on the dendritic branch, of a capping component selected from at least one of the group consisting of an acid, an acid anhydride, an acid chloride, an isocyanate and a silicon-containing material.

Accordingly, it is possible to react the secondary hydroxyl groups, in a capping reaction, with acids, acid anhydrides, acid chlorides, isocyanates, and silicon-containing materials, which modifies the dendritic or branched structure. Silicon-containing materials include those that can subsequently react with water to further cross-link the dendritic compositions. Acid anhydrides or chlorides including but not limited to those of acrylic or methacrylic acid, itaconic acid, benzoic or other aromatic acids, maleic acid, may be used. The use of such capping materials offers an opportunity to change the glass transition temperature (Tg) of the resultant linoleum composition and the cross-link density of the cured linoleum-based compositions.

In some embodiments, each dendritic branch is cross-linked to a further dendritic branch by a cross-linking substituent derived from reaction, with a hydroxyl functionality on the cross-linked dendritic branches, of a cross-linking component selected from at least one of the group consisting of a melamine, an isocyanate and a silicon-containing material.

Accordingly, in some embodiments, the composition is curable via a dual curing process comprising a first curing step reacting together the pendant olefin functionality and a second curing step reacting a different functionality in the a dendritic or branched composition, the first and second curing steps being alternative or additive and carried out in any order or simultaneously. The use of these hydroxyl containing dendritic or branched materials can provide such a dual cure mechanism for linoleum based compositions. It is possible to use the secondary hydroxyls to cross-link these compositions. Cross-linking agents for reacting with hydroxyl groups are well known and include but are not limited to methoxymethyl melamine types, for example melamine formaldehyde, and isocyanates. It is also possible to have at least a proportion of the total cross-linking of these linoleum materials occurring either before or during combination with the pre-oxidation step of linoleum manufacture, or added directly to an oxidized linoleum cement formulation before processing to form the final linoleum product. There are also applications where such dual cure materials have uses without combining with linseed oil compositions.

In another embodiment, dual cure compositions may be formulated by incorporating reactive olefin groups into the dendritic structures, for example by reacting unsaturated precursors such as, for example, acrylic acid, maleic acid, or itaconic acid, or similar unsaturated molecules, with the primary and/or dendritic branches. These compositions have the added ability to be peroxide cured either in the linoleum process or with subsequent heating.

Additionally, reacting the epoxidized polyfunctional core materials with less than stoichemetric amounts of the acids containing reactive olefin groups can be used. For example, reacting itaconic acid with epoxidized linseed oil such that a viscous material is produced having some pendant epoxy groups can be employed. These residually-epoxidized materials can be further reacted through their epoxy groups with hydroxyl groups produced during oxidation of linseed oil. These compositions can be processed into a linoleum formulation containing a reactive peroxide initiator. Subsequent processing/heating of the composition provides a radical induced cross-linking of the itaconic acid reactive olefin functional group. It is apparent to those skilled in the art that other reactive diacids could be substituted with another reactive site to provide a dual cure composition. It is also apparent to those skilled in the art that pendant acid functional groups can be employed depending upon the ratio of epoxy to acid functional groups. It is also to be understood that different polyfunctional core materials can be employed in these dendritic or branched structures. For example other multi functional epoxy materials can be employed, including but not limited to triglycidyl isocyanurate and fatty acid esters of pentaerythritol. The polyfunctional core material should be compatible with epoxidation, acid/epoxy reaction, and esterification. These polyfunctional core materials may include other polyfunctional alcohols, in addition to glycerin which is employed to form the triglyceride exemplified above. For example bio-based pentaerythritol, a tetra functional alcohol may be employed as the precursor to the polyfunctional core material.

The invention will now be further illustrated with reference to the following non-limiting Examples.

EXAMPLES

Example 1

The epoxidized triglyceride of linoleic acid is reacted with linoleic acid to produce Composition I, as described above, which is a symmetrical, level 1 dendritic type molecule.

Example 2

Epoxidized linseed oil is reacted with linoleic acid to produce Composition II, as described above, which is an asymmetrical, level 1 branched molecule

Example 3

The secondary hydroxyl groups of Compositions I and II are further reacted with linoleic acid to form polyester Compositions III and IV, as described above, respectively.

Example 4

Composition III is epoxidized to produce a dendritic epoxy molecule, identified herein as Composition V.

Example 5

Composition V is then epoxidized to produce a branched epoxy molecule, identified herein as Composition VI.

Example 6

Compositions V and VI are further reacted with linoleic acid as in Examples 1 and 2, thereby producing respective level 2 dendritic or branched molecules, identified herein as Compositions VII and VIII respectively.

Example 7

Composition III is mixed with linseed oil and the mixture subjected to a pre-oxidation step conventionally employed in linoleum production to increase viscosity and produce a binder for the preparation of linoleum cement. The time to reach the desired viscosity is reduced, as compared to conventional linoleum production, due to the presence of Composition III.

Example 8

The product of Example 7 is compounded and processed into a linoleum product in a process conventionally employed in linoleum production. The curing time required for achieving the typical desired linoleum properties is substantially reduced, as compared to conventional linoleum production, due to the presence of Composition III.

Example 9

Composition III is added directly to a mixture of oxidized linseed oil for use in the production of a linoleum composition. After mixing, the composition is processed, in a process conventionally employed in linoleum production, to produce a linoleum product. The curing time required for achieving the desired properties is substantially reduced, as compared to conventional linoleum production, due to the presence of Composition III.

Example 10, 11, 12

Composition IV is utilized instead of composition III is a similar manner as described in Examples 7, 8, and 9. Again significant reduction is cure time is observed.

Example 13

Composition II containing hydroxyl groups is mixed with linseed oil and subjected to a pre-oxidation step within a Bedford reactor. After completion of the oxidation step, a reactive melamine cross-linker (Cymel 303) is added to the mixture and a linoleum cement formulation produced. Subsequently, the processed linoleum formulation is heated and fused producing a "cured" product with good physical properties.

Example 14

Composition II containing hydroxyl groups is mixed with pre-oxidized linseed oil and a reactive melamine cross-linker (Cymel 303) is added. The mixture is compounded into a linoleum formulation and processed as described in Example 13. Again, a cured product having good physical properties is obtained.

Example 15

Epoxidized linseed oil is reacted with a less than stoichiometric amount of itaconic acid to produce a viscous, liquid with pendant epoxy groups. This reactive material is mixed into oxidized linseed oil and a reactive peroxide initiator added. A linoleum cement formulation is compounded and processed. At the elevated temperature during heating, the residual epoxy groups react with hydroxyl groups including those of the oxidized linseed composition, and the decomposition of the peroxide polymerizes the olefin functional groups of the itaconic acid. These type systems can be considered dual cure and processed as such. A cured product having good physical properties is obtained.

The invention claimed is:

1. A linoleum composition including a dendritic substituent comprising:
   (i) a polyfunctional core including a plurality of primary branches extending from the core, the polyfunctional core derived from a polyglyceride of one or more $C_{16}$ to $C_{20}$ unsaturated fatty acids; and
   (ii) a plurality of first dendritic branches extending from the plurality of primary branches, and
   (iii) a plurality of second dendritic branches pendant from the first dendritic branches, each secondary dendritic branch having an unsaturated functionality;
   wherein the number of second dendritic branches is greater than the number of first dendritic branches.

2. The linoleum composition of claim 1, wherein the polyglyceride comprises a triglyceride.

3. The linoleum composition of claim 1, wherein the one or more $C_{16}$ to $C_{20}$ unsaturated fatty acids comprise at least one $C_{18}$ fatty acid.

4. The linoleum composition of claim 1, wherein the polyglyceride is derived from linseed oil and comprises derivatives of linoleic, oleic and alpha-linoleic acid.

5. The linoleum composition of claim 1, wherein the first dendritic branch is derived from at least one second unsaturated fatty acid selected from a C16 to C20 unsaturated fatty acid.

6. The linoleum composition of claim 5, wherein the at least one second unsaturated fatty acid is a $C_{18}$ unsaturated fatty acid.

7. The linoleum composition of claim 6, wherein the at least one second unsaturated fatty acid is linoleic acid.

8. The linoleum composition of claim 1, wherein the first dendritic branch is derived from at least one third unsaturated fatty acid and having an unsaturated functionality, and the second dendritic branch being derived from at least one fourth unsaturated fatty acid and having an unsaturated functionality.

9. The linoleum composition of claim 8, wherein at least one or both of the third and fourth unsaturated fatty acids is a C16 to C20 unsaturated fatty acid.

10. The linoleum composition of claim 9, wherein at least one or both of the third and fourth unsaturated fatty acids is linoleic acid.

11. The linoleum composition of claim 1, wherein the second dendritic branch has a hydroxyl functionality.

12. The linoleum composition of claim 1, wherein each dendritic branch has a tertiary substituent derived from reaction, with a hydroxyl functionality on the dendritic branch, of a capping component selected from at least one of the group consisting of an acid, an acid anhydride, an acid chloride, an isocyanate and a silicon-containing material.

13. The linoleum composition of claim 1, wherein there are 2 to 4 of the first dendritic branches per primary branch of the polyfunctional core.

14. The linoleum composition of claim 13, wherein there are 2 to 4 of the second dendritic branches per first dendritic branch.

15. A linoleum composition comprising a dendritic substituent having the formula:

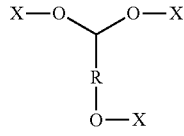

wherein
X=—C(O)—(CH$_2$)$_7$—CH(OH)—CH(OY)—CH$_2$—CH(OH)—CH(OY)—(CH$_2$)$_4$—CH$_3$
Y=—C(O)—(CH$_2$)$_7$—CH(OH)—CH(OZ)—CH$_2$—CH(OH)—CH(OZ)—(CH$_2$)$_4$—CH$_3$; and
Z=—C(O)—(CH$_2$)$_7$—CH=CH—CH$_2$—CH=CH—(CH$_2$)$_4$—CH$_3$;
wherein R is derived from a polyglyceride of one or more C$_{16}$ to C$_{20}$ unsaturated fatty acids.

16. A linoleum composition comprising a dendritic substituent having the formula:

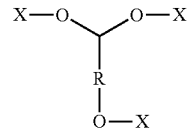

wherein
X=—C(O)—(CH$_2$)$_7$—CH(OY)—CH(OY)—CH$_2$—CH(OY)—CH(OY)—(CH$_2$)$_4$—CH$_3$
Y=—C(O)—(CH$_2$)$_7$—CH(OZ)—CH(OZ)—CH$_2$—CH(OZ)—CH(OZ)—(CH$_2$)$_4$—CH$_3$; and
Z=—C(O)—(CH$_2$)$_7$—CH=CH—CH$_2$—CH=CH—(CH$_2$)$_4$—CH$_3$;
wherein R is derived from a polyglyceride of one or more C$_{16}$ to C$_{20}$ unsaturated fatty acids.

17. The linoleum composition of claim 1, wherein each dendritic branch is cross-linked to a further dendritic branch by a cross-linking substituent derived from reaction, with a hydroxyl functionality on the cross-linked dendritic branches, of a cross-linking component selected from at least one of the group consisting of a melamine, an isocyanate and a silicon-containing material.

* * * * *